US012569663B2

(12) United States Patent
Acharya et al.

(10) Patent No.: US 12,569,663 B2
(45) Date of Patent: Mar. 10, 2026

(54) CONNECTOR SAFETY SHIELD

(71) Applicant: Becton, Dickinson and Company, Franklin Lakes, NJ (US)

(72) Inventors: Vineeth Acharya, Udupi (IN); Shashwat Jain, Indore (IN); Muralikrishna Menon, Bangalore (IN); Praveen Nalawade, Belagavi (IN); Senthilkumar Rakkiyappan, Tamilnadu (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 670 days.

(21) Appl. No.: 18/070,872

(22) Filed: Nov. 29, 2022

(65) Prior Publication Data

US 2024/0173534 A1     May 30, 2024

(51) Int. Cl.
A61M 39/16       (2006.01)
A61M 39/20       (2006.01)

(52) U.S. Cl.
CPC .......... A61M 39/162 (2013.01); A61M 39/20 (2013.01)

(58) Field of Classification Search
CPC .... A61M 39/162; A61M 39/20; A61M 39/16; A61M 39/165; A61M 39/0247; A61M 39/1011; A61M 2039/0258; A61M 2039/0285; A61M 2039/0288; A61M 2039/1066; A61M 2210/12
See application file for complete search history.

(56) References Cited

U.S. PATENT DOCUMENTS

| | | | |
|---|---|---|---|
| 5,694,978 A * | 12/1997 | Heilmann | A61M 39/20 138/89 |
| 8,574,202 B2 | 11/2013 | Alheidt | |
| 8,740,856 B2 | 6/2014 | Quinn et al. | |
| 9,283,369 B2 * | 3/2016 | Ma | A61M 39/162 |
| 9,480,833 B2 | 11/2016 | Hoang et al. | |
| 10,376,686 B2 * | 8/2019 | Burkholz | A61M 39/162 |

(Continued)

*Primary Examiner* — Catherine S Williams
(74) *Attorney, Agent, or Firm* — The Webb Law Firm

(57)                    ABSTRACT

A connector safety shield configured to engage a needle free connector comprises a push cap slidably mounted on an external enclosure cap that encloses a spray chamber containing disinfectant that can be pushed multiple times out of perforations in the bottom of the spray chamber and onto the distal end of the needle free connector by action of a stopper mounted in the spray chamber and operably connected to the push cap. The connector safety shield also comprises a bottom enclosure cap that can engage the needle free connector and thus lock the connector safety shield onto the needle free connector. A hinge connecting the bottom enclosure cap and the assembly of the external closure cap, spray chamber, and push cap allows the assembly of the external closure cap, spray chamber, and push cap to be rotated out of connection with the needle free connector such that the needle free connector can be connected to another device or object such as a syringe or other vascular access device. The assembly of the external closure cap, spray chamber, and push cap can be rotated back into connection with the needle free connector and used to spray the distal end of the needle free connector with disinfectant once the other device or object such as a syringe or other vascular access device is removed.

18 Claims, 13 Drawing Sheets

(56) References Cited

U.S. PATENT DOCUMENTS

| | | | | |
|---|---|---|---|---|
| 10,850,085 | B2 | 12/2020 | Tekeste | |
| 12,440,660 | B2 * | 10/2025 | Prasad | A61L 2/22 |
| 2010/0050351 | A1 * | 3/2010 | Colantonio | A61M 39/20 |
| | | | | 15/104.93 |
| 2012/0302997 | A1 * | 11/2012 | Gardner | A61M 39/20 |
| | | | | 604/533 |
| 2013/0338644 | A1 * | 12/2013 | Solomon | A61M 39/162 |
| | | | | 604/535 |
| 2014/0366914 | A1 * | 12/2014 | Kerr | A61B 1/122 |
| | | | | 15/104.93 |
| 2018/0214684 | A1 * | 8/2018 | Avula | A61M 39/162 |
| 2019/0076885 | A1 | 3/2019 | Ryan et al. | |
| 2019/0232039 | A1 * | 8/2019 | Erekovcanski | A61M 5/3134 |
| 2022/0273931 | A1 * | 9/2022 | Jiang | A61M 39/20 |
| 2024/0149039 | A1 * | 5/2024 | Prasad | A61M 39/162 |
| 2024/0173530 | A1 * | 5/2024 | Prasad | A61M 39/16 |
| 2024/0173531 | A1 * | 5/2024 | Kumar | A61M 39/1011 |
| 2024/0173533 | A1 * | 5/2024 | Kumar | A61M 39/162 |
| 2024/0173535 | A1 * | 5/2024 | Prasad | A61M 39/16 |
| 2024/0173537 | A1 * | 5/2024 | Nalawade | A61M 39/162 |
| 2024/0173538 | A1 * | 5/2024 | Nalawade | A61L 2/18 |
| 2024/0198075 | A1 * | 6/2024 | Raj | A61M 39/16 |

* cited by examiner

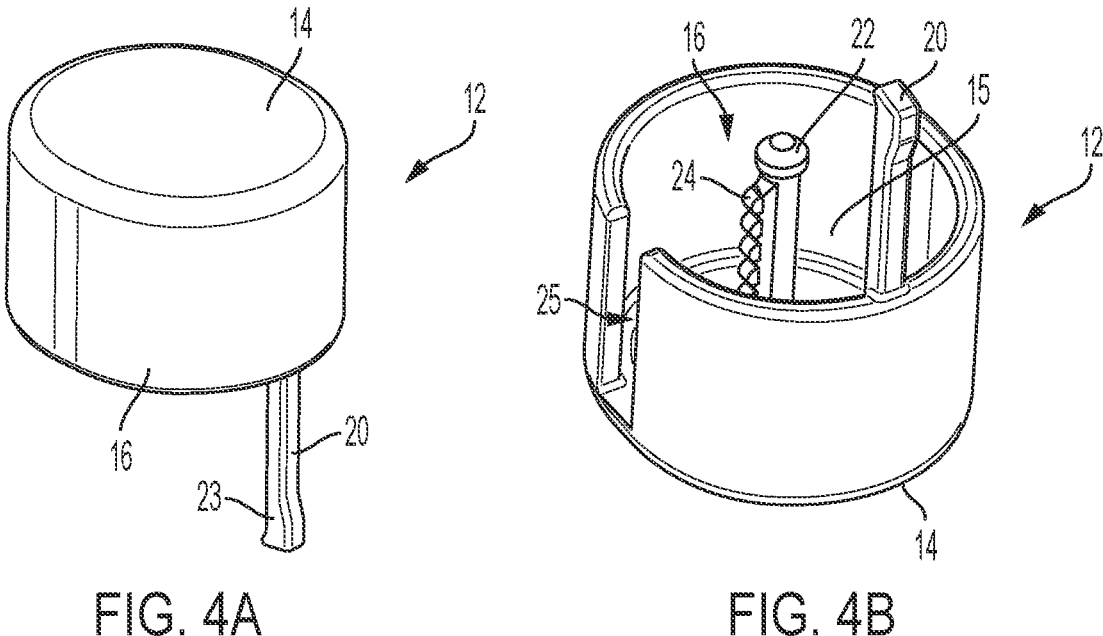
FIG. 4A                                    FIG. 4B
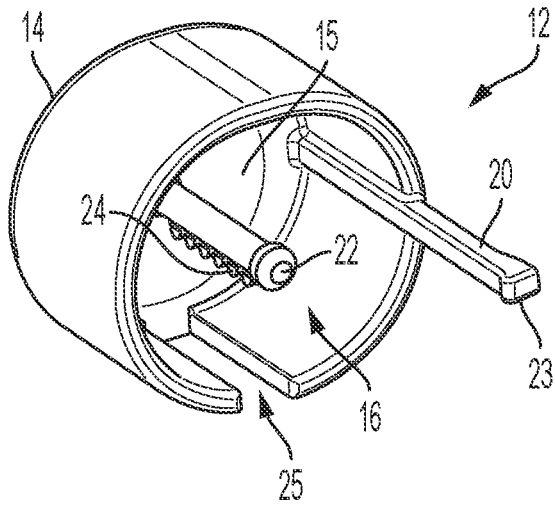
FIG. 4C

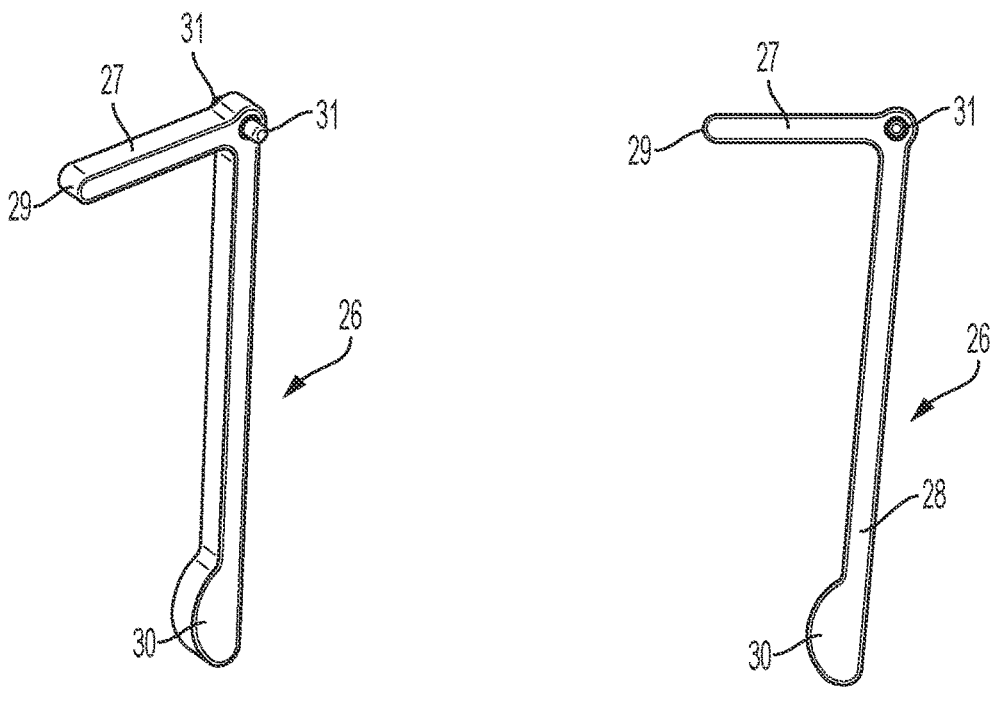
FIG. 9A
FIG. 9B
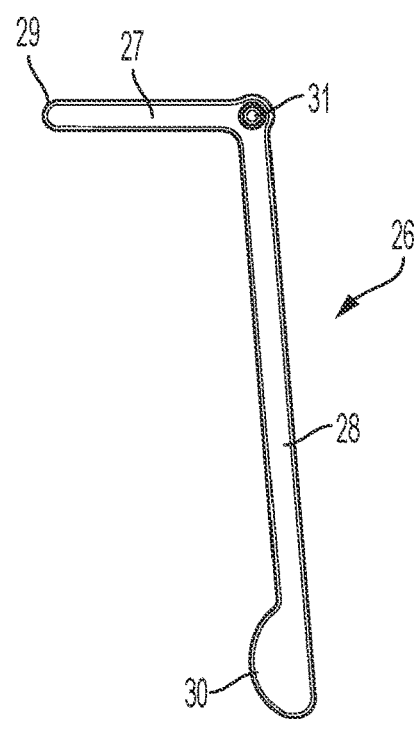
FIG. 9C

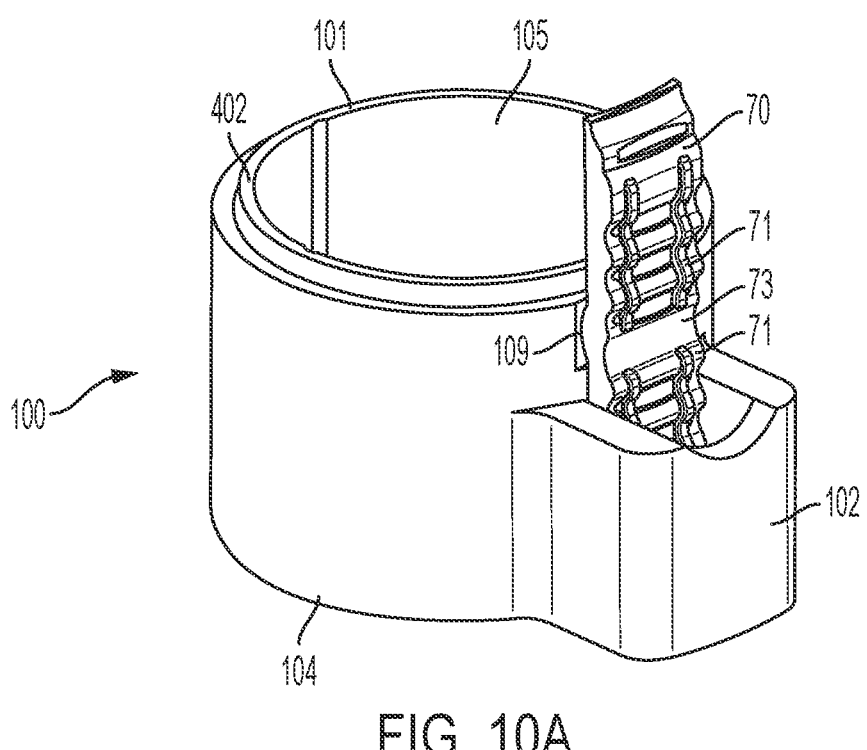
FIG. 10A
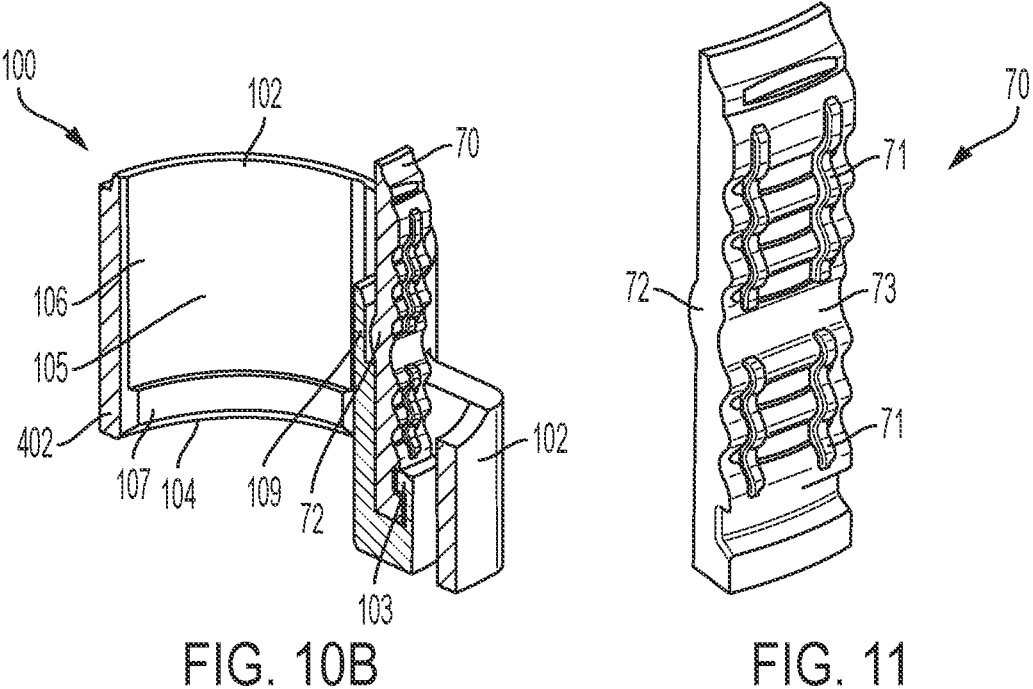
FIG. 10B                    FIG. 11

CONNECTOR SAFETY SHIELD

BACKGROUND OF THE INVENTION

Field of the Invention

The present disclosure relates generally to caps for medical connectors and, in particular, to a connector safety shield comprising a medical cap with a spray mechanism within the cap configured to be attached to needle free connectors for sealing, cleaning, and disinfecting portions of the needle free connectors.

Description of Related Art

Vascular access devices (VADs) are commonly used medical devices, which can include intravenous (IV) catheters, such as peripheral catheters or central venous catheters, and include needle free connectors (NFCs). If not properly maintained or if exposed to a non-sterile environment, the NFCs and VADs can become contaminated, sealed with blood clots, and/or can spread infection. Further, bacteria and other microorganisms may gain entry into a patient's vascular system from NFCs and access hubs, ports, or valves upon connection to the VAD to deliver a fluid or pharmaceutical to a patient. For example, when a patient goes to the restroom, the nurse may disconnect the IV line thereby exposing the NFC to contamination while the patient is in or travelling to or from the restroom. Therefore, each NFC or access hub (or port/valve or connection) configured for attachment to a VAD is associated with some risk of transmitting a catheter related bloodstream infection (CRBSI) to a patient.

Many medical facilities implement sterile practices and protocols to ensure that VADs and NFCs, access hubs or ports are used properly and do not become sealed or infected. These protocols often include sterilizing the NFCs, access hubs, ports, and VADs, as well as flushing the catheter with a flush solution prior to use. Specifically, VAD standards of practice usually recommend flush procedures be performed after catheter placement, before fluid infusion, and before and after drug administration, blood sampling, transfusions, and/or administration of parenteral nutrition. Standards of practice can also require that NFCs, access hubs, ports, and valves be capped with caps, including disinfection caps, when not in use, to prevent microbial ingress into the hub, port, or valve and to sterilize areas of the NFC, hub, port, or valve that contact the VAD. Some caps may cover the luer end of NFCs, access hubs, or ports of VADs but may have slits or openings that may lead to CRBSI. Disinfection caps are disposable cap devices that contain an amount of cleaning or disinfecting solution for sterilizing portions of the NFC, port, hub, or valve.

Some examples of disinfection caps are known. For example, U.S. Pat. No. 9,480,833, entitled "Antimicrobial IV Access Cap," which is incorporated herein by reference in its entirety, discloses a cap having an inner surface for retaining an antimicrobial agent configured to engage a portion of the NFC or access port of a VAD. U.S. Patent Application Publication No. 2019/0076885 entitled "Integrated Cleaning and Disinfection Device, System, and Method," which is incorporated herein by reference in its entirety, discloses a single piece device which enables medical clinicians to clean and disinfect both an injection port for a NFC IV connector and a VAD catheter hub.

However, there is a need for a disinfection cap that includes an active mechanism that can be used multiple times to disinfect the NFC or port area of a VAD.

SUMMARY OF THE INVENTION

According to an aspect of the disclosure, a connector safety shield configured to engage a NFC of a VAD that includes a spray mechanism within the connector safety shield to disinfect the NFC surface or contact area multiple times after the connector safety shield is opened. The connector safety shield can be further configured to enclose the complete distal end of the NFC. In another aspect of the disclosure, the spray mechanism can be further configured to be used multiple times but to be locked after reaching a maximum usage time.

In accordance with an embodiment of the present invention, a connector safety shield configured to engage a connector includes a push cap having a closed top, an open bottom, and a sidewall extending between the top and the bottom. The push cap further includes a side arm extending downward through the open bottom and a center arm extending from the center of the closed top to the center of the open bottom; a second cap slidably connected to the push cap and including a top, an open bottom, and a sidewall extending between the top and the bottom for enclosing a spray chamber including an open top and a perforated bottom disposed in the second cap. The top includes an opening configured to allow the center arm of the push cap to extend through the second cap and engage a stopper located within the spray chamber that seals the open top of the spray chamber; and, a third bottom cap that removably connects to the second cap including an open top, an open bottom and a sidewall with an exterior surface extending between the top and bottom that is configured to engage the connector to lock the connector safety shield to the connector, wherein the side arm of the push cap engages a hinge connected to sidewall of the third bottom cap and a lock handle is operably engaged with the second cap and the sidewall of the third bottom cap to operably connect the push cap to the second cap and the third bottom cap.

In accordance with an embodiment of the present invention, the disinfectant includes chlorhexidine digluconate (CHG) and isopropyl alcohol (IPA).

In accordance with an embodiment of the present invention, the push cap, second cap, and third bottom cap include a rigid thermoplastic polymer having at least one of polyester, polycarbonate, polypropylene, polyethylene, polyethylene terephthalate, or acrylonitrile butadiene styrene.

In accordance with an embodiment of the present invention, the hinge includes a plurality of teeth for engaging the side arm of the push cap and includes a thinner center section that enables the hinge to bend in a direction away from the third bottom cap such that the push cap, second cap, and spray chamber are disengaged from the connector and the third bottom cap.

In accordance with an embodiment of the present invention, the hinge includes an elastomer.

In accordance with an embodiment of the present invention, the side arm of the push cap engages the teeth of the hinge to urge the hinge against the sidewall of the second cap thereby further operably connecting the push cap to the second cap and operably connecting the push cap to the hinge and the third bottom cap.

In accordance with an embodiment of the present invention, the push cap is configured to be pushed in a downward direction towards the third bottom cap multiple times thereby pushing the center arm of the push cap and the stopper into the spray chamber causing the disinfectant in the spray chamber to spray out of perforated bottom of the spray chamber and onto the connector multiple times.

In accordance with an embodiment of the present invention, the hinge is made of an elastomer, the stopper is made of an isoprene, the spray chamber is made of high-density polyethylene, and the first push cap, the second cap, the third bottom cap, and the lock handle are made of polypropylene.

In accordance with an embodiment of the present invention, the connector safety shield further includes a filter positioned adjacent the perforated bottom of the spray chamber to block air and prevent leakage of disinfectant.

In accordance with an embodiment of the present invention, a connector safety shield is configured to enclose a needle free connector having a distal end, wherein the connector safety shield includes a spray chamber holding disinfectant, wherein the spray chamber is configured to spray disinfectant on the distal end of the needle free connector.

In accordance with an embodiment of the present invention, the connector safety shield further includes a first cap configured to engage the distal end of the needle free connector, a second cap operably connected to the first cap configured to enclose and position the spray chamber adjacent to the distal end of the needle free injector, and a third cap operably connected to the first cap, the second cap, and the spray chamber configured to push the disinfectant out of the spray chamber and onto the distal end of the needle free connector.

In accordance with an embodiment of the present invention, the disinfectant includes chlorhexidine digluconate (CHG) and isopropyl alcohol (IPA).

In accordance with an embodiment of the present invention, the spray chamber includes a bottom surface with a plurality of perforations through which the disinfectant is sprayed on the distal end of the needle free connector.

In accordance with an embodiment of the present invention, the connector safety shield further includes a lock handle pivotally mounted to the second cap and configured to engage the first cap to lock the second cap to the first cap, a side arm fixedly connected to the third cap, and a hinge fixedly connected to the first cap having a plurality of teeth configured to engage the side arm to flexibly connect the third cap to the first cap.

In accordance with an embodiment of the present invention, the connector safety shield further includes a stopper positioned within the spray chamber to seal the disinfectant in the spray chamber and to push the disinfectant in the spray chamber towards the distal end of the connector; and a center arm fixedly connected to the center of the third cap and configured to extend into the spray chamber and engage the stopper such that movement of the third cap towards the second cap and the spray chamber moves the stopper within the spray chamber thereby pushing the disinfectant in the spray chamber towards the distal end of the connector.

In accordance with an embodiment of the present invention, the spray chamber further includes a bottom surface with a plurality of perforations through which the disinfectant is pushed by the movement of the stopper such that the disinfectant is sprayed on the distal end of the needle free connector.

In accordance with an embodiment of the present invention, the hinge further includes a plurality of teeth configured to engage the side arm to flexibly connect the third cap to the first cap, and a thinner center section that enables the hinge to bend in a direction away from the first cap such that the second cap, the third cap, and the spray chamber are disengaged from the connector such that the first cap is still connected to the connector.

In accordance with an embodiment of the present invention, the connector safety shield is configured to allow the third cap to move in incremental steps towards the second cap and the spray chamber through engagement of the side arm with the plurality of the teeth on the hinge to thereby move the stopper in incremental distances within the spray chamber allowing the disinfectant to be sprayed on the distal end of the connector.

In accordance with an embodiment of the present invention, the hinge is made of an elastomer, the stopper is made of an isoprene, the spray chamber is made of high-density polyethylene, and the first cap, the second cap, the third cap, and the lock handle are made of polypropylene.

In accordance with an embodiment of the present invention, a connector safety shield configured to engage a connector includes a first cap having a closed top, an open bottom, and a sidewall extending between the top and the bottom defining an annular opening, a second cap slidably engaged with said first cap comprising an open bottom defining an annular opening and a top defining an opening there through and a sidewall extending between the top and the bottom, a spray chamber with an open top sealed by a stopper and a perforated bottom disposed within said second cap, a third cap with an open top, an open bottom, and a sidewall extending between the top and the bottom defining a cylindrical opening wherein the third cap engages the connector and the bottom of the second cap, a hinge having threads mounted to the third cap and operably connected to the first cap by a side arm extending from the sidewall of the first cap, and a center arm extending from the closed top of the first cap extending through the opening in the top of the second cap to engage the stopper positioned within the spray chamber configured to push disinfectant through the perforated bottom of the spray chamber onto the connector.

BRIEF DESCRIPTION OF THE DRAWINGS

FIG. 4A is a perspective view of the top portion of the push cap of the connector safety shield of FIG. 2A and FIG. 3, according to an aspect of the present disclosure.

FIG. 4B is a perspective view of a bottom portion of the push cap of FIG. 4A.

FIG. 4C is another perspective view of a bottom portion of the push cap of FIG. 4A and FIG. 4B.

5

Figures 5A, 5B:
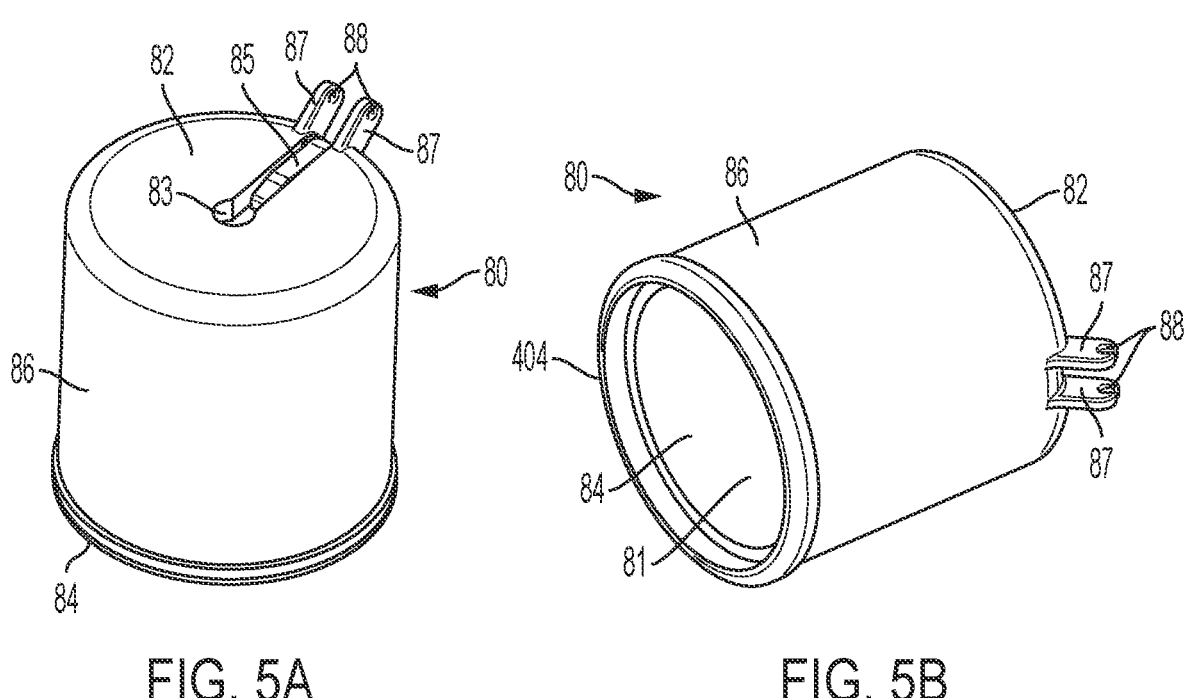
FIG. 5A is a perspective view of a top and side portion of an external enclosure cap of the connector safety shield of FIG. 3, according to an aspect of the present disclosure.

FIG. 5B is a perspective view of a bottom and side portion of the external enclosure cap of FIG. 5A, according to an aspect of the present disclosure.

Figure 5C:
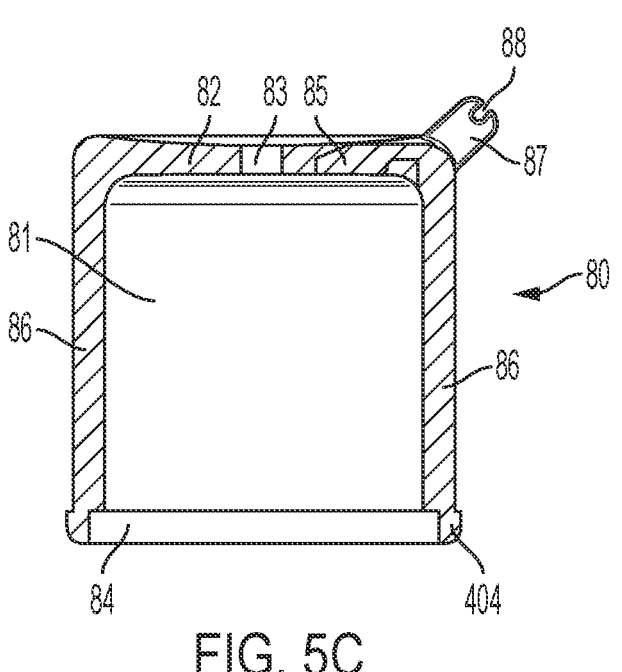

FIG. 5C is a cross-section view of the external enclosure cap of FIG. 5A, according to the present disclosure.

Figure 3:
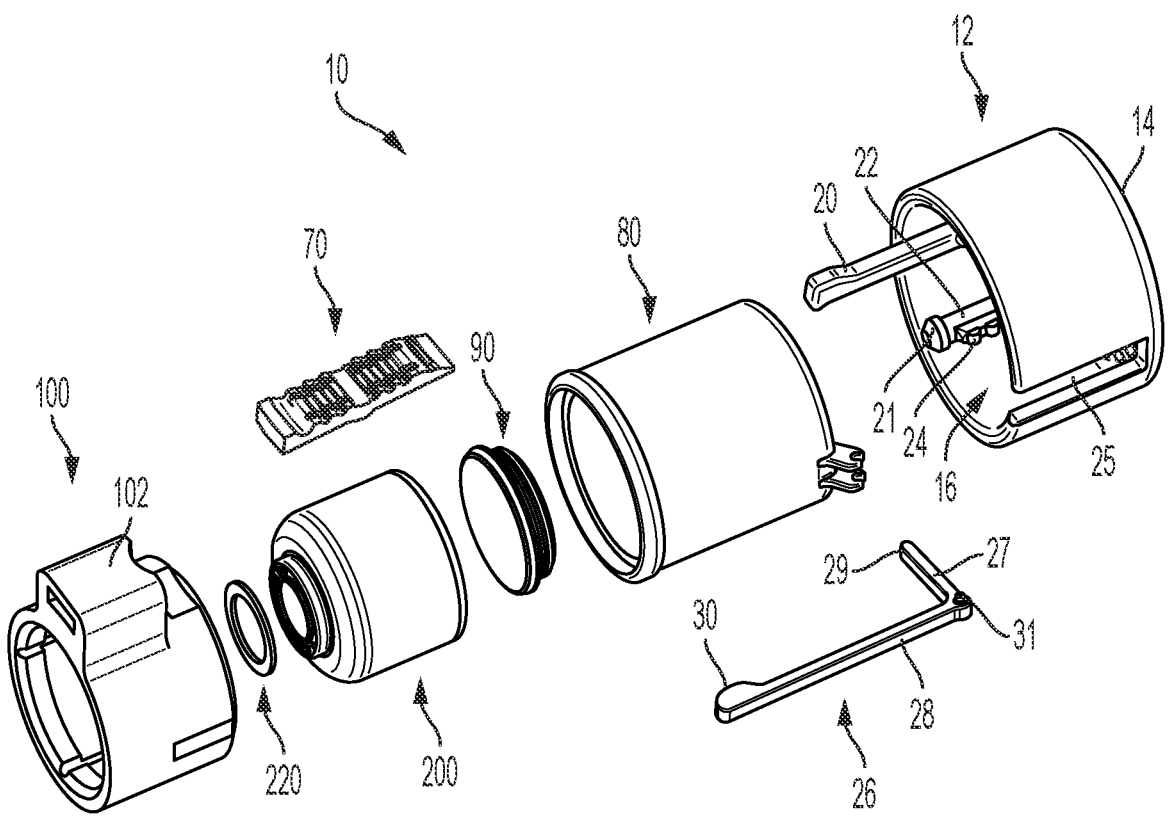
FIG. 3 is an exploded perspective view of the components of the connector safety shield according to an aspect of the present disclosure.
Figures 6A, 6B, 6C, 6D, 7A, 7B, 8:
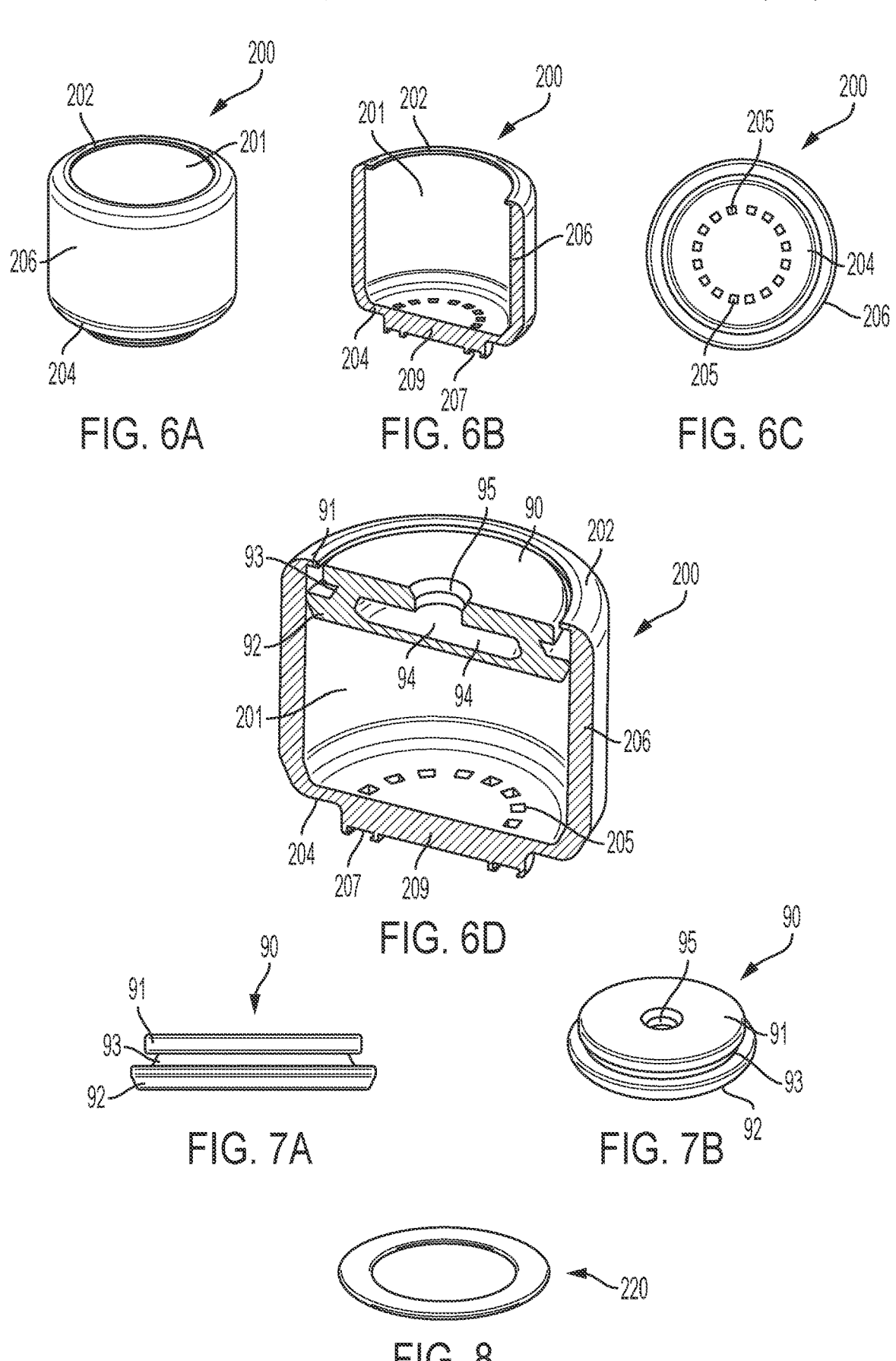

FIG. 6A is a perspective view of a spray chamber of the connector safety shield of FIG. 3, according to an aspect of the present disclosure.

FIG. 6B is cross-section view of the spray chamber of FIG. 6A, according to an aspect of the present disclosure.

FIG. 6C is bottom view of the spray chamber of FIG. 6A, according to an aspect of the present disclosure.

FIG. 6D is cross-section view of the spray chamber of FIG. 6A assembled with a stopper of FIG. 7A and FIG. 7B, according to an aspect of the present invention.

FIG. 7A is a side view of a stopper of the connector safety shield of FIG. 3, according to an aspect of the present disclosure.

FIG. 7B is a perspective view of a stopper of the connector safety shield of FIG. 3, according to an aspect of the present disclosure.

FIG. 8 is enlarged perspective view of a filter of the connector safety shield of FIG. 3, according to an aspect of the present disclosure.

FIG. 9A is a perspective view of a lock handle the connector safety shield of FIG. 3, according to an aspect of the present disclosure.

FIG. 9B is a side view of the lock handle of FIG. 9A, according to an aspect of the present disclosure.

FIG. 9C is a side view of the lock handle of FIG. 9A after one arm is moved in an angled direction, according to an aspect of the present disclosure.

FIG. 10A is a perspective view of the bottom enclosure cap of the connector safety shield of FIG. 3, according to an aspect of the present disclosure.

FIG. 10B is a cross-section view of the bottom enclosure cap the connector safety shield of FIG. 3, according to an aspect of the present disclosure.

FIG. 11 is a perspective view of the hinge of the connector safety shield of FIG. 3, according to an aspect of the present disclosure.

Figure 1A:
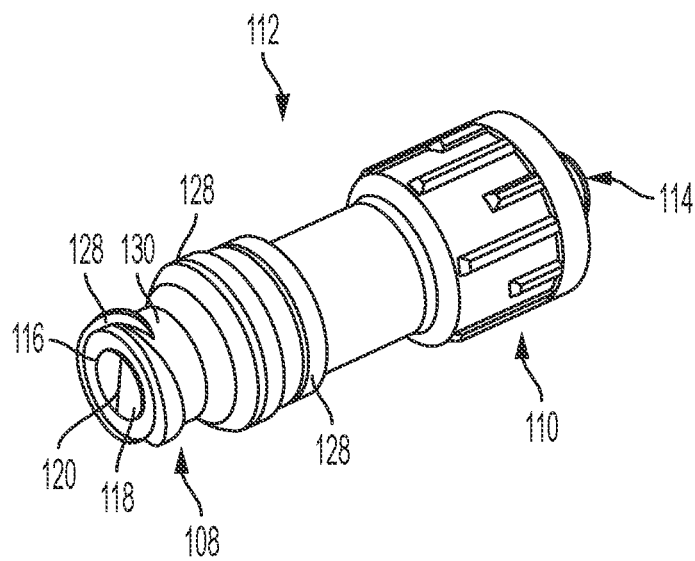
FIG. 1A is a perspective view of an exemplary medical connector or NFC, as is known in the prior art.
Figures 12A, 12B, 12C, 12D:
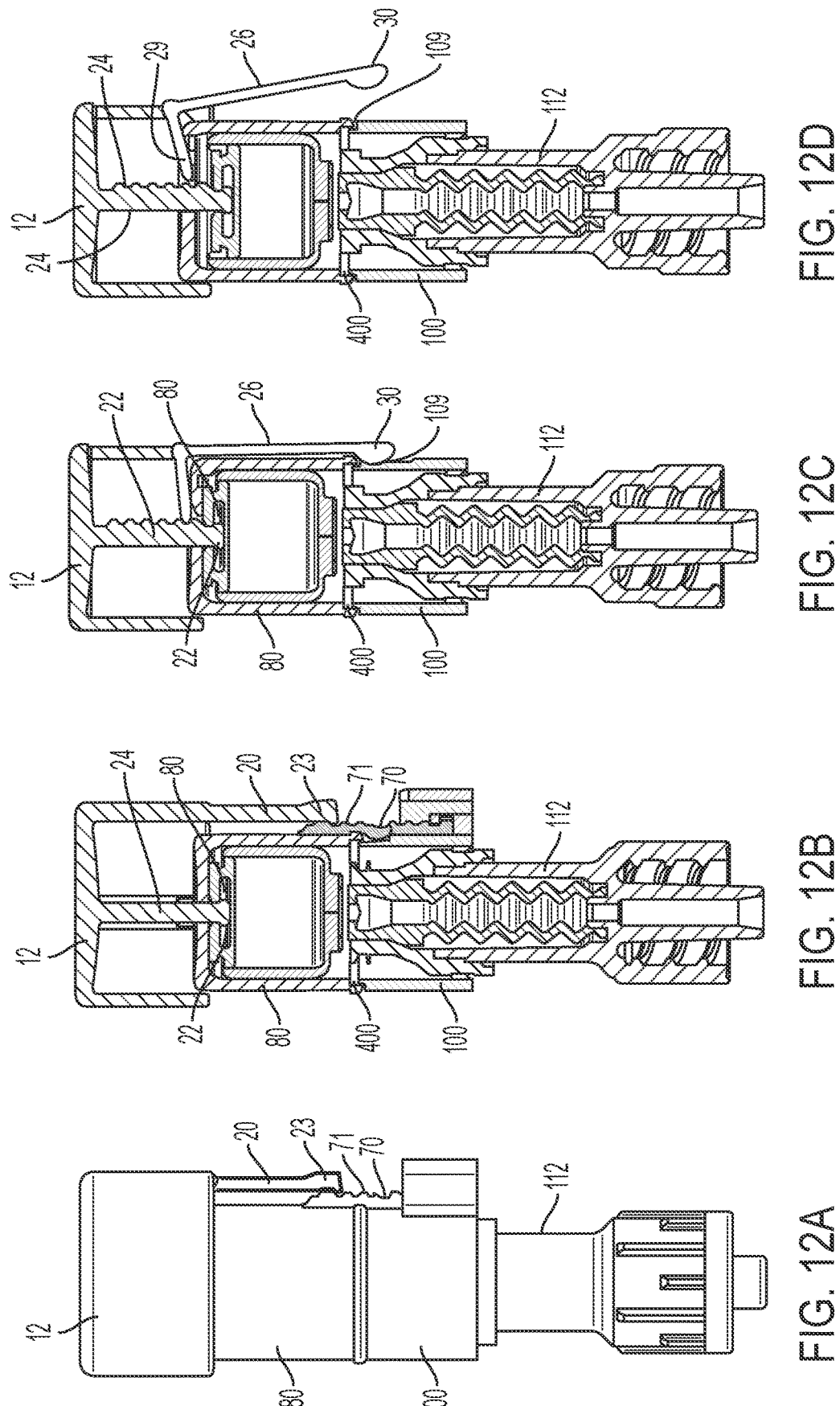

FIG. 12A is a perspective view of a connector safety shield according to an aspect of the present disclosure connected to the prior art NFC of FIG. 1A.

FIG. 12B is a cross-section view of the connector safety shield of FIG. 12A connected to the prior art NFC of FIG. 1A showing a cap arm of the push cap engaged with the hinge, according to an aspect of the present disclosure.

FIG. 12C is a cross-section view of the connector safety shield of FIG. 12A connected to the prior art NFC of FIG. 1A showing a lock handle engaged with the bottom enclosure cap, according to an aspect of the present disclosure.

FIG. 12D is a cross-section view of the connector safety shield of FIG. 12A connected to the prior art NFC of FIG. 1A showing a lock handle disengaged with the bottom enclosure cap, according to an aspect of the present disclosure.

Figures 13A, 13B, 14:
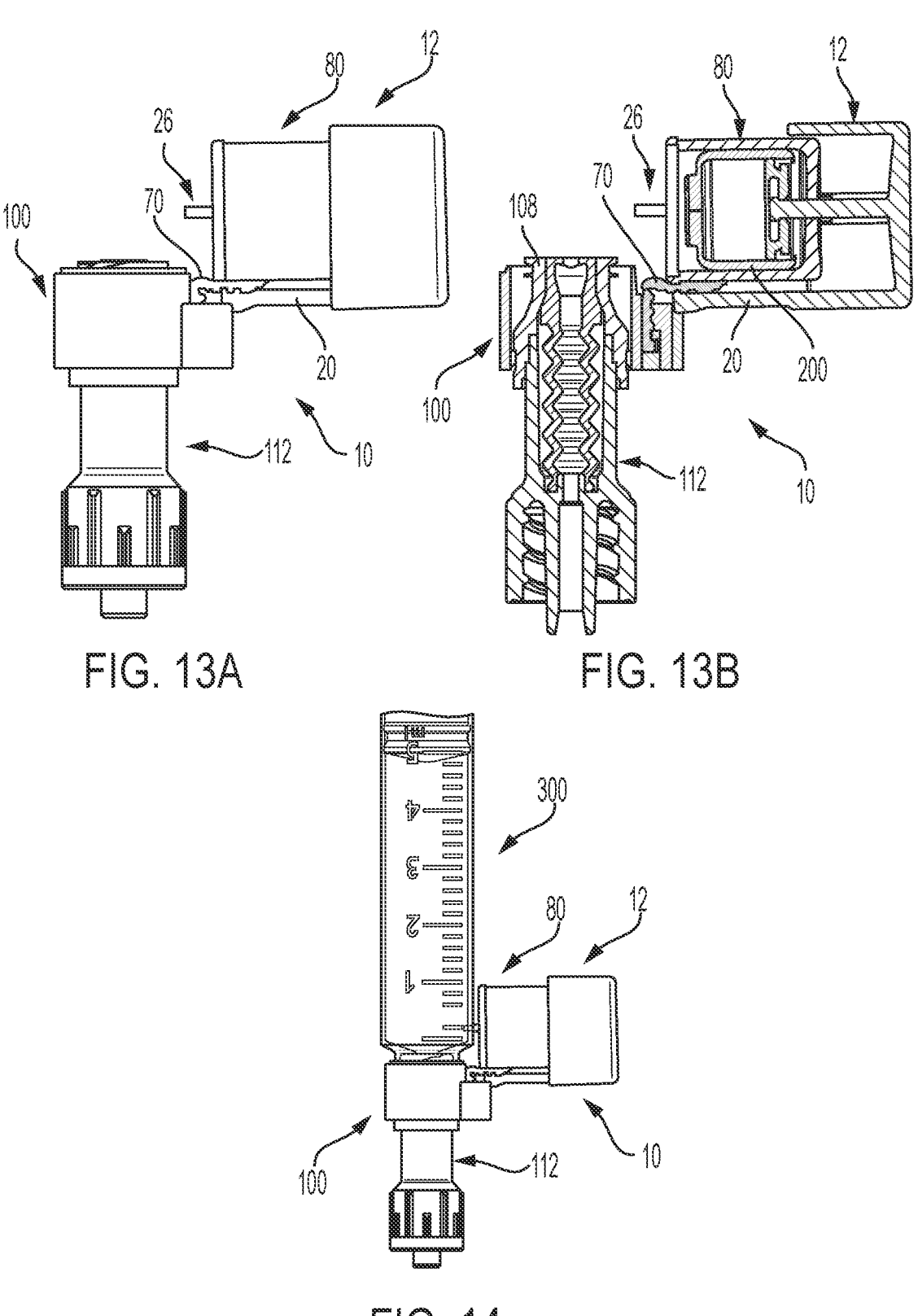

FIG. 13A is a perspective view of a connector safety shield according to an aspect of the present disclosure connected to the prior art NFC of FIG. 1A showing the push cap of FIG. 4A and the external enclosure of FIG. 5A disengaged from the bottom enclosure cap of FIG. 10A, according to an aspect of the present disclosure.

FIG. 13B is a cross-section view of a connector safety shield according to an aspect of the present disclosure connected to the prior art NFC of FIG. 1A showing the push cap of FIG. 4A and the external enclosure of FIG. 5A disengaged from the bottom enclosure cap of FIG. 10A, according to an aspect of the present disclosure.

FIG. 14 is a perspective view of a connector safety shield according to an aspect of the present disclosure connected to the prior art NFC of FIG. 1A showing the push cap of FIG. 4A and the external enclosure of FIG. 5A disengaged from the bottom enclosure cap of FIG. 10A and the NFC connected to a syringe, according to an aspect of the present disclosure.

Figures 15A, 15B, 15C, 15D, 15E:
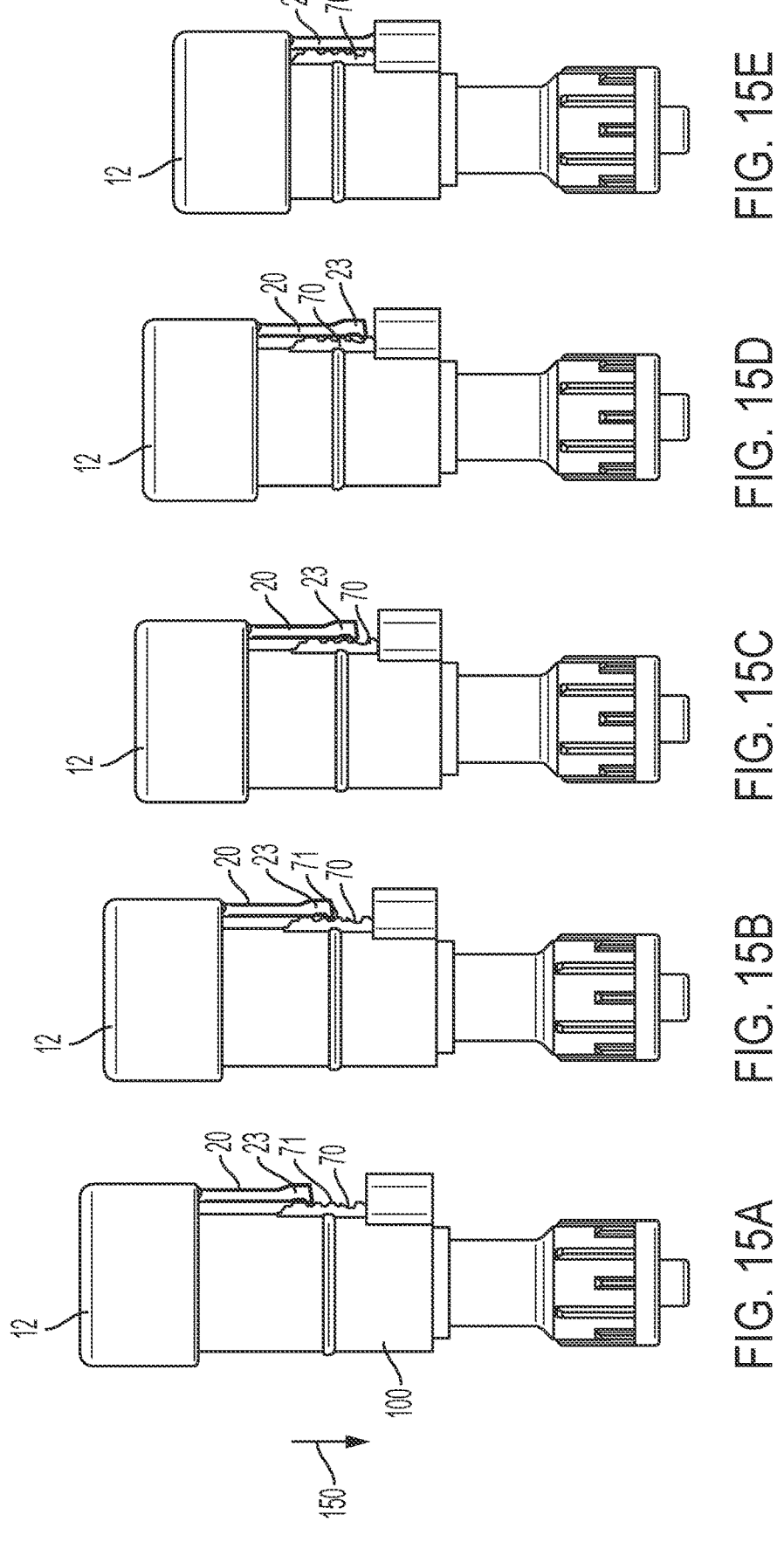

FIG. 15A is a perspective view of a connector safety shield according to an aspect of the present disclosure connected to the prior art NFC of FIG. 1A prior to use of the connector safety shield to disinfect the NFC.

FIG. 15B is a perspective view of a connector safety shield according to an aspect of the present disclosure connected to the prior art NFC of FIG. 1A after a first push of the push cap of the connector safety shield to disinfect the NFC.

FIG. 15C is a perspective view of a connector safety shield according to an aspect of the present disclosure connected to the prior art NFC of FIG. 1A after a second push of the push cap of the connector safety shield to disinfect the NFC.

FIG. 15D is a perspective view of a connector safety shield according to an aspect of the present disclosure connected to the prior art NFC of FIG. 1A after a third push of the push cap of the connector safety shield to disinfect the NFC.

FIG. 15E is a perspective view of a connector safety shield according to an aspect of the present disclosure connected to the prior art NFC of FIG. 1A after a fourth and final push of the push cap of the connector safety shield to disinfect the NFC, thereby locking movement of the push cap.

Figure 16:
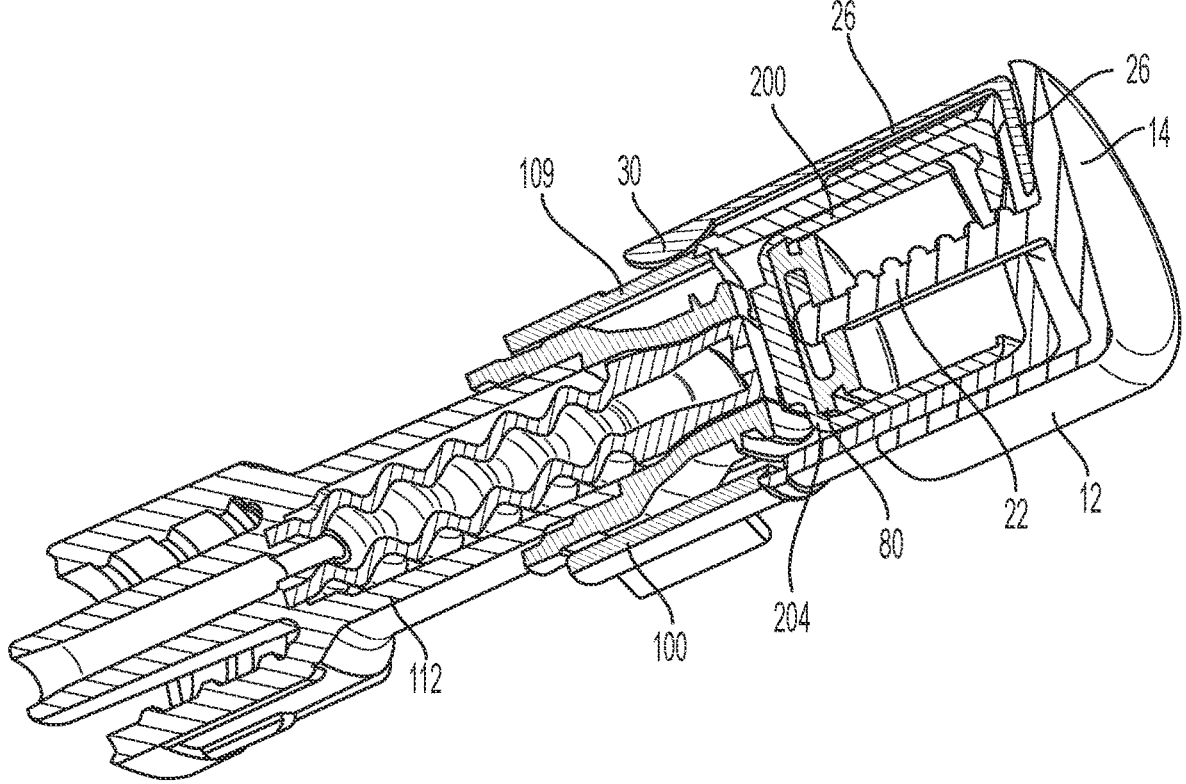

FIG. 16 is a cross-section view of a connector safety shield according to an aspect of the present disclosure connected to the prior art NFC of FIG. 1A after the push cap of the connector safety shield has been depressed the maximum amount to disinfect the NFC, thereby locking movement of the push cap as shown in FIG. 15E.

DESCRIPTION OF THE INVENTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left". "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure is directed to a connector safety shield 10 configured to be connected to different types of medical connectors 112, such as NFCs or hubs, ports, or valves for a VAD, to prevent the connector, NFC, or VAD from being contaminated by, for example, microbes, debris, or other contaminants. The connector safety shield 10 can be configured to clean or disinfect the surface of the connector 112 or NFC, ensuring that the connector 112 or NFC remains sterile prior to use. The connector safety shield 10 can be configured to engage or be connected to different sizes, configurations, or types of medical connectors 112 or NFCs. For example, the connector safety shield 10 can be configured to engage or be connected to NFCs or connectors 112 of different designs, configurations, and sizes. In particular, the connector safety shield 10 can be configured for use with NFCs or connectors 112 having different arrangements of threads, such as threads with different inner or outer diameters or threads with different thread widths (e.g., threads having different widths at the crest and/or root of the thread).

Figure 1B:
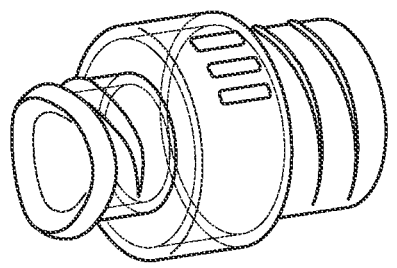
FIG. 1B is a cap, as is known in the prior art.

As used herein, a needle free connector or "NFC" refers to a connector 112 comprising an opening or port 116 that is configured to be inserted in a tube or opening of another object or device having an inner diameter that is larger than an outermost diameter of the distal portion 108 of the connector 112 in order to connect the object or device to the NFC or connector 112. The connector 112 can comprise an elongated tubular distal portion 108 with a cover or septum 118 over the opening 116. An exemplary connector 112 including a septum 118 with a slit 120 is shown in FIG. 1A. The connector 112 can be configured to be connected to or engage various types of objects or devices such as cap 150 as is known in the prior art as shown in FIG. 1B. The connector or NFC can comprise a proximal portion that comprises a male connector 110 comprising an elongated member, such as a tubular member or stem 114, configured to be inserted in a tube or opening having an inner diameter that is smaller than an outermost diameter of the male connector 110.

As used herein, a "luer connector" refers to a connector that includes a tapered portion (i.e., a luer taper) for creating a friction engagement between a tapered stem 114 or elongated member of a male luer connector 110 and a tapered cavity. Specifically, the male luer connector 110 includes a tapered stem 114 or elongated member having a tapered outer surface. A female luer connector can include a tapered cavity configured to receive and engage the tapered stem or elongated member to connect a male luer connector to the female luer connector.

Figure 2A:
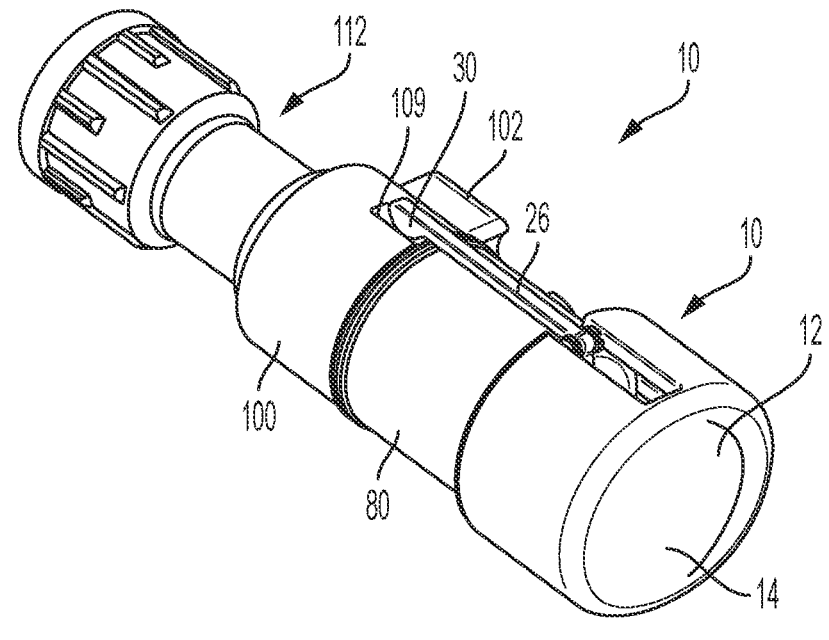
FIG. 2A is a perspective view of a connector safety shield according to an aspect of the present disclosure connected to a prior art NFC.
Figure 2B:
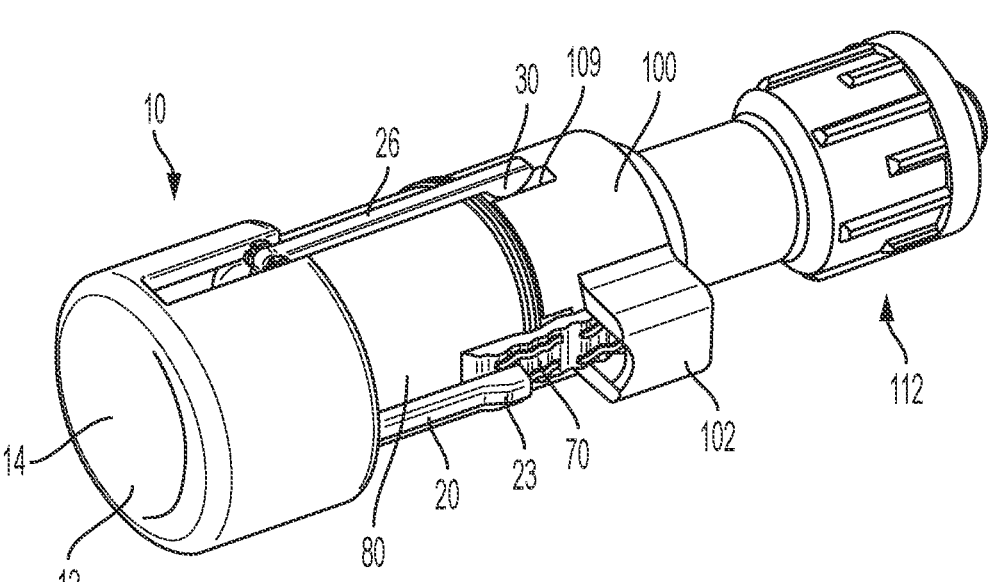
FIG. 2B is another perspective view showing the connector safety shield of FIG. 2A according to an aspect of the present disclosure connected to a prior art NFC.
Figure 2C:
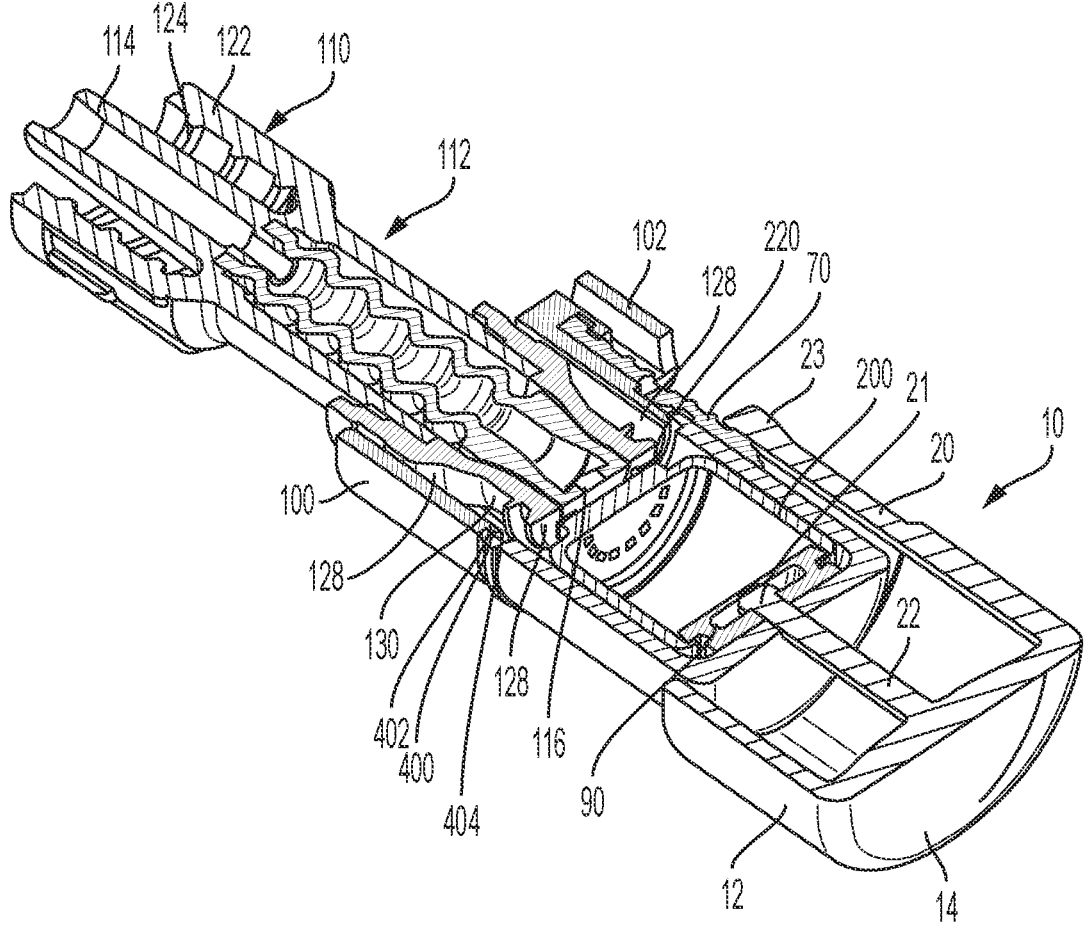
FIG. 2C is cross-sectional view of the connector safety shield of FIG. 2A connected to a prior art NFC, according to an aspect of the present disclosure.

The distal end 108 and the male connector 110 of the NFC or connector 112 can include engaging structures, such as threads, for connecting the NFC 112 to other objects or devices. For example, as shown in FIG. 2C, the male luer connector 110 can include an annular shield 122 extending about the tapered stem 114 or elongated member. The annular shield 122 can include threads 124 on an inner surface 126 of the shield 122 configured to engage corresponding threads on an outer surface of a female luer connector (not shown). The NFC or connector 112 can comprise a female luer connection. For example, as shown in FIG. 1A, the NFC or connector 112 includes the threads 128 extending from the outer surface 130 positioned to engage threads on the inner surface of another object or device. Twisting the NFC or connector 112 can cause the corresponding threads 124, 128 to engage threads on other objects or devices such as a syringe or a connector for tubing.

The connector safety shield 10 of the present disclosure can be configured to engage a variety of different configurations and orientations of NFCs or connectors 112, such as different types of needleless luer connectors, and can be used for all types of female luer connections. As will be appreciated by those skilled in the art, there are numerous different commercially available medical devices, such as hubs, ports, and valves, which include different variations of connectors 112. The connector safety shield 10 of the present disclosure can be configured to adapt or deform so that it can be secured to numerous different types and sizes of NFCs or connectors 112. For example, the connector safety shield 10 of the present disclosure can also be configured to cover different connector designs including, without limitation, the BD Q-Syte™, BD MaxZero™, BD MaxPlus™, and SmartSite™ needle free connectors by Becton Dickinson and Company. The connector safety shield 10 can also be configured to be connected to connectors by other manufactures.

FIGS. 2A-2C and FIG. 3 illustrate an exemplary connector safety shield 10 configured to engage and/or to be connected to NFCs or connectors 112. In particular, the connector safety shield 10 can be configured to be used with NFCs or connectors 112 with different dimensions and/or different arrangements of threads 128 on the outer surface of the distal end portion 108 of the NFC or connector 112. In some examples, the connector safety shield 10 of the present disclosure is configured to cover and seal the distal end portion 108 of the NFC or connector 112 to prevent microbial ingress into the connector 112. In addition, the connector safety shield 10 can include components, such as a spray chamber holding disinfectant, for cleaning and disinfecting portions of the connector 112.

As shown in FIGS. 2A-2C and FIG. 3, the connector safety shield 10 may comprise in one embodiment of the invention a push cap 12, a lock handle 26, an external enclosure cap 80, a stopper 90, a hinge 70, a spray chamber 200, a filter 220, and a bottom enclosure cap 100. The lock handle 26 is assembled with the push cap 12 and the push cap 12 is slidably connected along the outside surface of the external enclosure cap 80. The stopper 90 and spray chamber 200 may be disposed within the external enclosure cap 80 and the filter 220 is seated on the bottom surface of the spray chamber 200. One end of the hinge 70 is disposed within a pocket 102 attached to the outer surface of the bottom enclosure cap 100.

The push cap 12 may comprise a closed top 14, an open annular bottom 16, and a sidewall 18 extending between the top 14 and the bottom 16 as shown in FIGS. 4A-4C. The push cap 12 can be generally a cup-shaped container defining a cylindrical space 15. In some examples, the push cap 12, along with other components of the connector safety shield 10, can be disposable, often formed from thin sheets or layers of an inexpensive material, such as a hard plastic, which can be disposed of after a single use. In some examples, the push cap 12 can include a side arm 20 connected or molded into the interior of the sidewall 18 for engaging or moving on a flexible hinge 70 and a central arm 22 connected or molded onto the interior or bottom surface of the closed top 14 at the center of the closed top 14 and extending into and through the interior bottom of the cup-shaped push cap 14. The bottom tip 21 of the central arm 22 of the push cap 12 can in some examples have a wider diameter than the central arm 22 or can be formed into a disk or bolbous shape as shown in FIG. 2C, FIG. 3 and FIGS. 4B-4C. The open bottom 16 and cylindrical space 15 are dimensioned and configured to receive at least the top portion of the external enclosure cap 80.

The push cap 12 may also comprise a plurality of teeth or threads 24 on a central arm 22 of the push cap 12 configured to engage one end 29 of the generally L-shaped lock handle 26 for stopping movement of and locking the push cap 10 in a second position after it is pushed from a first position. As shown in FIGS. 9A-9B, the lock handle 26 comprises a first arm 27 connected perpendicular to a second longer arm 28 wherein the first end 29 of the first arm 27 is configured to engage the central arm 22 of the push cap 12 and the free end of the second longer arm 28 comprises a bulb 30 configured to move into a channel or groove 109 formed or machined on the outer surface of the bottom enclosure cap 100 as shown in FIGS. 2A-2B. As also shown in FIGS. 9A-9B, the lock handle 26 includes a boss structure 31 disposed on either side of the lock handle 26 for pivotally attaching or connecting the lock handle 26 to the external closure cap 80 such that lock handle 26 can be disposed within the rectangular-shaped side opening 25 of the push cap 12 when the push cap 12 is depressed. The lock handle 26 can be constructed of a flexible material so that the second longer arm 28 can bend or move to an angle greater than 90 degrees relative to the first arm 27 of the locking handle 26 as shown in FIG. 9C.

As shown in FIGS. 5A-5C, the external closure cap 80 may comprise a generally closed top 82, an open annular bottom 84, and a sidewall 86 extending between the top 82 and the bottom 84 defining a generally cup-shaped container and a cylindrical space 81 defined within the interior of the cap 80. The generally closed top 82 comprises an opening 83 that extends through the top to the bottom of the top 82 and a key slot 85 that is formed, molded or machined into the exterior top surface of the generally closed top 82. Two lock handle support arms 87 extend at an angle which can be generally 45 degrees in one embodiment from the junction of the top 82 and the sidewall 86. The lock handle support arms 87 comprise slots or holes 88 at their outermost tip for engaging or supporting the boss structure 31 disposed on both sides of the locking handle 26 such that the locking handle 26 can pivot about the axis formed through the side of the slots or holes 88 and boss structure 31 when they are engaged. The open bottom 84 and the cylindrical space 81 of the external closure cap 80 are dimensioned and configured to receive the spray chamber 200 as shown for example in FIG. 2C and FIG. 16.

As shown in FIGS. 6A-6D, the spray chamber 200 may comprise on open annular top 202, a bottom 204, and a sidewall 206 extending between the top 202 and the bottom 204 defining a generally cup-shaped container and a cylindrical space 201 defined within the interior of the spray chamber 200 to hold the disinfectant. The bottom 204 may contain a plurality of openings or perforations 205 for transferring the disinfectant from the interior cylindrical space 201 of the spray chamber 200 to the connector 112 surface when the push cap 12 is depressed. The size, number, and locations of the perforations 205 can be determined by the flow rate of disinfectant required or desired and the volume of disinfectant that is required or desired to be dispensed. In one example, if the cross-sectional area of the cylindrical space 201 within the interior of the spray chamber 200 is 54 mm², the area of the openings or perforations 205 would need to be 3.75 mm² to dispense 0.45 ml of disinfectant in 1 second assuming a pressure of 10 psi is applied to the disinfectant in the spray chamber 200 thereby generating a flow rate of 12.96 ml/sec/cm². In one example, the bottom 204 of the spray chamber 200 may comprise a thicker portion 209 and an annular grove 207 is formed on or machined into the bottom surface of the thicker portion 209. The perforations 205 are formed or machined into the thicker portion 209 of the bottom 204 within the annular grove 207. The annular grove 207 is configured to hold or retain an annular filter 220 to block air and prevent leakage of disinfectant from the perforations 205. In one example, the filter 220 as shown in FIG. 8 can be a 5-micron filter and hydrophobic. The connector safety shield 10 comprising a spray chamber 200 filled with disinfectant and sealed by the stopper 90 is designed to provide disinfectant action on the connector 112 for multiple times without contamination.

The spray chamber 200 is configured to contain disinfectant before it is assembled into the connector safety shield 10. In one example, the disinfectant can comprise a solution of chlorhexidine digluconate (CHG) and isopropyl alcohol (IPA). In other examples, the disinfectant can be an antimicrobial, anti-fungal, antibacterial, or antiviral solution that cleans and sterilizes surface of the connector 112. In particular, the disinfectant is used to clean and disinfect surfaces of the distal end portion 108, opening or port 116, and septum 118 of the connector 112.

As shown in FIGS. 7A-7B and FIG. 6D, the stopper 90 may comprise a top circular disk 91, a bottom circular disk 92 and a sidewall 93 extending between the top disk 91 and the bottom disk 92 forming a hollow interior space or pocket 94 between the top disk 91 and the bottom disk 92. An opening or hole 95 is formed or machined into and through the top disk 91. The stopper 90 is initially assembled into the top of the spray chamber 200 as shown in FIG. 6D. The stopper 90 is held in position in the spray chamber 200 by a friction fit against the interior of the sidewall 206 of the spray chamber 200 in the interior cylindrical space 201 of the spray chamber 200. The stopper 90 is positioned and fitted within the spray chamber 200 to contain the disinfectant and prevent leakage of the disinfectant through the open top 202 of the spray chamber 200. The stopper 90 acts the same as a syringe mechanism which performs the function of pushing the disinfectant out of the interior cylindrical space 201 of the spray chamber 200 in which it is held through the perforations 205 in the bottom 204 of the spray chamber 200 and through the filter 220 and onto the surface of the NFC or connection 112. The stopper 90 is pushed through the interior of the spray chamber 200 by the action of the wider or bolbous bottom tip 21 of the central arm 22 of the push cap 12 which can be inserted through the hole 95 in the top circular disk 91 of the stopper 90 such that it is locked in place within the pocket 94 in the stopper 90 as shown for example in FIG. 2C such that the movement of the push cap 12 and the central arm 22 when it is pushed also moves the stopper 90 through the interior space 201 of the spray chamber 200.

As shown in FIGS. 10A-10B, the bottom enclosure cap 100 can be a tubular structure comprising an open annular top 101, an open annular bottom 104, and a sidewall 106 extending between the top 101 and the bottom 104 defining an open cylindrical space 105 defined within the interior of the cap 100. The bottom enclosure cap further includes an inwardly extending protrusion 107 extending inwardly from the inner surface of the sidewall 106 of the cap 100 positioned adjacent to the open bottom 103 configured to engage the NFC or connection 112 as shown most clearly for example in FIGS. 12B-12C. The protrusion 107 can be an annular ridge or rib. A rigid pocket 102 with an open top and a partially closed bottom is attached to or formed with the outer surface of the sidewall 106 of bottom enclosure cap 100 for supporting and locking in place the hinge 70. A retaining hook or tab 103 is molded into the bottom of the interior of the pocket 102 to engage or snap onto the teeth 71 on the bottom portion of the hinge 102 and lock the hinge 102 in place shown in FIG. 10B. A channel or groove 109 is formed or machined on the outer surface of the sidewall 106 of bottom enclosure cap 100 as shown in FIGS. 2A-2B for holding or retaining the bulb 30 at the free end of the longer arm 28 of the lock handle 26. The open annular top 101 and side wall 106 of the bottom enclosure cap 100 may be configured to be removably engaged with the open annular bottom 84 and sidewall 86 of the external enclosure cap 80 so as to create a seal or cover around the distal tip 108 of the connector 112. Specifically, the bottom enclosure cap 100 may comprise an extended annular projection 402 extending upward from the open annular top 101 and side wall 106 of the bottom enclosure cap 100 as best seen in FIGS. 10A-10B that is of a smaller diameter than an extended annular projection 404 extending from the open annular bottom 84 and sidewall 86 of the external enclosure cap 80 as best seen in FIGS. 5B-5C such that the extended annular projections engage each other so as to cover the junction 400 between the bottom enclosure cap 100 and the external enclosure cap 80 as can best be seen in FIG. 2C and FIGS. 12B-12D.

As shown in FIG. 11, the hinge 70 can be an elastomer hinge in some examples and can include a plurality of teeth 71 comprising generally rounded protrusions formed or machined on one side of the hinge 70. A bump or rounded protrusion 72 is formed into the opposite side of the hinge 70 that can engage a depression 109 on the sidewall 106 of bottom enclosure cap 100 to further position the hinge 70. The hinge 70 assists the movement of the side arm 20 of the push cap 12 which can be configured on its bottom or free end 23 to engage the teeth 71 of the hinge 70 as shown in FIGS. 2B-2C. The hinge 70 also supports the opening of the connector safety shield 10 at the junction between the bottom enclosure cap 100 and the external enclosure cap 80 as shown in FIGS. 13A-13C. The hinge 70 can be formed from a single piece of elastomer material such that it can bend at least at a ninety (90) degree angle relative to its initial position along an axis at its center portion 73 as shown in FIGS. 13A-13B. To facilitate the bend, the center portion 73 which is formed to have smaller thickness of elastomer material as shown in FIG. 11. In one example, the hinge 70 comprises a single piece or component. In other examples, the hinge 70 could comprise two or more pieces or components that are joined for example by a mechanical hinge or other structures that allow the hinge to pivot about an axis such as for example a structure and arrangement similar to the boss structure 31 and lock handle support arms 87 used to support the lock handle 26 such that the lock handle 26 can pivot about an axis.

In order to connect the connector safety shield 10 to a NFC or connector 112, such as a female connector 112 shown in FIGS. 12A-12B, the practitioner first removes any packaging from the connector safety shield 10. The practitioner then moves the connector 112 toward and into the open bottom 104 of the bottom enclosure cap 100, as shown in FIGS. 12B-12D as well as FIG. 2C, causing the threads 128 of the connector 112 to move towards the inwardly extending protrusion 107 extending inwardly from the inner surface of the sidewall 106 of the bottom enclosure cap 100 positioned adjacent to the open bottom 103 configured to engage the NFC or connection 112 The practitioner then applies pressure to the connector 112, causing the distal end portion 108 of the connector 112 to move through protrusion 107 until the distal end of the connector 108 is pushed adjacent to and up against the bottom surface of the thicker portion 209 of the bottom 204 of the spray chamber 200. For example, threads 128 of the connector 112 can press against and deform the protrusion 107, thereby allowing the connector 112 to move through the open bottom 104 of the bottom enclosure cap 100, as shown in FIGS. 12B-12D. The distal end 108 of the connector 112 is thus pressed against and sealed by the bottom 209 of the spray chamber and the filter 220. Once threads 128 of the connector 112 move past the protrusion 107, the protrusion can deflect radially inward to retain the distal end portion 108 of the connector 112 within the cylindrical space 105 of the bottom enclosure cap 100.

As shown in FIGS. 12A-12B, the end 23 of the side arm 20 of the push cap 12 engages the teeth 71 on the hinge 30 to hold the push cap 12 in place and connected to the external enclosure cap 80 and the bottom enclosure cap 100. The end 22 of the central arm 24 of the push cap 12 engages with the stopper 80 to push the stopper 80 within the spray chamber 200. A shown in FIGS. 12C-12D, the end 30 of the lock handle 26 engages with the channel 109 on the outer surface of the bottom enclosure cap 100 to also hold the push cap 12 in place and connected to the external enclosure cap 80 and the bottom enclosure cap 100. The other end 24 of the lock handle 26 engages with teeth on the central arm 24. The lock handle 26 may be pivoted or moved at an angle to connector safety shield 10 so as to disengage the end 30 of the lock handle 26 from the channel 109 on the outer surface of the bottom enclosure cap 100 to allow for the push cap 12 to be depressed thereby pushing the stopper 80 within the spray chamber 200 given its engagement with the end 22 of the central arm 24 of the push cap 24.

The connector safety shield 10 is designed to remain in place on the connector 112 as the spray chamber 200 can be used multiple times to disinfect the connector 112. A VAD can be connected to the hub, port, or valve through the connector 112 with the connector safety shield 10 still attached to the NFC or connection 112. As shown in FIGS. 13A-13C, the upper portion of the connector safety shield 10 comprising the push cap 12 assembled with the external enclosure cap 80 and spray chamber 200 can be disengaged and rotated away from the distal end 108 of the connector 10 while the bottom enclosure cap 100 remains in place and engaged with the connector 112. For example, a syringe 300 can be then be connected to the distal end 108 of the connector 112 which is no longer completely covered or sealed by the connector safety shield 10.

As shown in FIGS. 15A-15C, the push cap 12 can be pushed or depressed in the downward direction towards the bottom enclosure cap 100 as indicated by the arrow 150. FIG. 15A shows the connector safety shield 10 connected to the NFC or connector 112 prior to use of the connector safety shield 10 to disinfect the connector 112 by pushing the push cap 100. FIG. 15B shows the connector safety shield 10 connected to the connector 112 after a first push of the push cap 12 of the connector safety shield 100 to spray disinfectant on the connecter 112. FIG. 15C shows the safety shield 10 according connected to the connector 112 after a second push of the push cap 12 of the connector safety shield 10 to disinfect the connector 112. FIG. 15D shows the safety shield 10 according connected to the connector 112 after a third push of the push cap 12 of the connector safety shield 10 to disinfect the connector 112. FIG. 15E shows the safety shield 10 according connected to the connector 112 after a fourth and final push of the push cap 12 of the connector safety shield 10 to disinfect the connector 112. FIG. 16 shows the connector safety shield 10 connected to the connection 112 after the push cap 12 of the connector safety shield 10 has been depressed the maximum amount to disinfect the connector 112, thereby locking movement of the push cap 12 as also shown in FIG. 15E. As the push cap 12 is pushed down each time, the end 23 of the side arm 20 of the push cap 12 is pushed along the teeth 71 of the hinge 70 such that the end 23 engages another one of the teeth 71 that is closer to the bottom 104 of the bottom enclosure cap 100 until the end 23 of the side arm 20 of the push cap 12 is in position lower and closer to the bottom 104 of the bottom enclosure cap 100 than the center 73 of the hinge 70 as shown in FIG. 15E.

Once the maximum usage time of the spray chamber 200 is reached, the operation of the connector safety shield 112 is locked as shown in FIG. 15E and FIG. 16. Specifically, when the push cap 12 has been depressed or pushed to the maximum extent possible such that the interior of the closed top 14 of the push cap 12 abuts up against the lock handle 26, the central arm 22 of the push cap 12 has pushed the stopper 80 up against the interior surface of the bottom 204 of the spray chamber 200, the end 30 of the lock handle 26 has engaged with the channel 109 on the outer surface of the bottom enclosure cap 100, and the end 23 of the side arm 20 of the push cap has pushed along the teeth 71 of the hinge 70 such that the end 23 has passed over and lower than the center 73 of the hinge 70, the push cap 12 and the hinge 70 are locked in place and will not allow further movement of the push cap 12. In order to remove the locked connector safety 10 from the connector 112, the practitioner can simply grip and pull the connector 112 out of engagement with the bottom enclosure cap 100 in a reverse of the procedure to insert the connector 112 into the connector safety shield 112. Alternatively, the practitioner can grip and pull the connector safety shield 112 off or away from the connector 112.

In some examples, components of the connector safety shield 10, including the push cap 12, lock handle 26, external enclosure cap 80, hinge 70, spray chamber 200, and bottom enclosure cap 100, can be molded parts formed by injection molding or other molding processes known in the art. The separately molded parts can be assembled together during manufacturing to provide a pre-packaged connector safety shield 10. Desirably, the pre-packaged connector safety shield 10 includes all components needed for sealing, cleaning, and sterilizing the connector 112. In some examples, the push cap 12, lock handle 26, external enclosure cap 80, hinge 70, spray chamber 200, and bottom enclosure cap 100 can be formed from a thermoplastic polymer material, such as polyester, polycarbonate, polypropylene, polyethylene, polyethylene terephthalate, or acrylonitrile butadiene styrene. The spray chamber may be formed from high-density polyethylene (HDPE). The lock handle 26 can be formed from a more flexible material since it is designed to flex or temporary bend or deform in normal usage. The stopper 90 may be formed of isoprene and the hinge 70 may be formed of an elastomer. All of the components of the connector safety shield 10 can be made of medical grade materials and can be sterilized using existing methods know in the art.

While examples of the connector safety shield 10 and methods of use of the present disclosure are shown in the accompanying figures and described hereinabove in detail, other examples will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A connector safety shield configured to engage a connector, comprising:

a push cap comprising a closed top, an open bottom, and a sidewall extending between the top and the bottom wherein the push cap further comprises a side arm extending downward through the open bottom and a center arm extending from the center of the closed top to the center of the open bottom;

a second cap slidably connected to the push cap and comprising a top, an open bottom, and a sidewall extending between the top and the bottom for enclosing a spray chamber comprising an open top and a perforated bottom disposed in the second cap wherein the top comprises an opening configured to allow the center arm of the push cap to extend through the second cap and engage a stopper located within the spray chamber that seals the open top of the spray chamber; and a third bottom cap that removably connects to the second cap comprising an open top, an open bottom and a sidewall with an exterior surface extending between the top and bottom that is configured to engage the connector to lock the connector safety shield to the connector, wherein the side arm of the push cap engages a hinge connected to sidewall of the third bottom cap and a lock handle is operably engaged with the second cap and the sidewall of the third bottom cap to operably connect the push cap to the second cap and the third bottom cap.

2. The connector safety shield of claim 1, wherein the disinfectant comprises chlorhexidine digluconate (CHG) and isopropyl alcohol (IPA).

3. The connector safety shield of claim 1, wherein the push cap, second cap, and third bottom cap comprise a rigid thermoplastic polymer comprising at least one of polyester, polycarbonate, polypropylene, polyethylene, polyethylene terephthalate, or acrylonitrile butadiene styrene.

4. The connector safety shield of claim 1, wherein the hinge comprises a plurality of teeth for engaging the side arm of the push cap and comprises a thinner center section that enables the hinge to bend in a direction away from the third bottom cap such that the push cap, second cap, and spray chamber are disengaged from the connector and the third bottom cap.

5. The connector safety shield of claim 4, wherein the hinge comprises an elastomer.

6. The connector safety shield of claim 4, wherein the side arm of the push cap engages the teeth of the hinge to urge the hinge against the sidewall of the second cap thereby further operably connecting the push cap to the second cap and operably connecting the push cap to the hinge and the third bottom cap.

7. The connector safety shield of claim 4, wherein the push cap is configured to be pushed in a downward direction towards the third bottom cap multiple times thereby pushing the center arm of the push cap and the stopper into the spray chamber causing the disinfectant in the spray chamber to spray out of perforated bottom of the spray chamber and onto the connector multiple times.

8. The connector safety shield of claim 1, wherein the hinge is comprised of an elastomer, the stopper is comprised of an isoprene, the spray chamber is comprised of high-density polyethylene, and the first push cap, the second cap, the third bottom cap, and the lock handle are comprised of polypropylene.

9. The connector safety shield of claim 1, further comprising a filter positioned adjacent the perforated bottom of the spray chamber to block air and prevent leakage of disinfectant.

10. A connector safety shield configured to enclose a needle free connector comprising a distal end, wherein the connector safety shield comprises:

a spray chamber holding disinfectant, wherein the spray chamber is configured to spray disinfectant on the distal end of the needle free connector;

a first cap configured to engage the distal end of the needle free connector;

a second cap operably connected to the first cap configured to enclose and position the spray chamber adjacent to the distal end of the needle free injector; and a third cap operably connected to the first cap, the second cap, and the spray chamber configured to push the disinfectant out of the spray chamber and onto the distal end of the needle free connector a lock handle pivotally mounted to the second cap and configured to engage the first cap to lock the second cap to the first cap;

a side arm fixedly connected to the third cap; and a hinge fixedly connected to the first cap comprising a plurality of teeth configured to engage the side arm to flexibly connect the third cap to the first cap.

11. The connector safety shield of claim 10, wherein the disinfectant comprises chlorhexidine digluconate (CHG) and isopropyl alcohol (IPA).

12. The connector safety shield of claim 10, wherein the spray chamber comprises a bottom surface with a plurality of perforations through which the disinfectant is sprayed on the distal end of the needle free connector.

13. The connector safety shield of claim 10, further comprising:

a stopper positioned within the spray chamber to seal the disinfectant in the spray chamber and to push the disinfectant in the spray chamber towards the distal end of the connector; and a center arm fixedly connected to the center of the third cap and configured to extend into the spray chamber and engage the stopper such that movement of the third cap towards the second cap and the spray chamber moves the stopper within the spray chamber thereby pushing the disinfectant in the spray chamber towards the distal end of the connector.

14. The connector safety shield of claim 13, wherein the spray chamber further comprises:

a bottom surface with a plurality of perforations through which the disinfectant is pushed by the movement of the stopper such that the disinfectant is sprayed on the distal end of the needle free connector.

15. The connector safety shield of claim 14, wherein the hinge further comprises:

a plurality of teeth configured to engage the side arm to flexibly connect the third cap to the first cap; and a thinner center section that enables the hinge to bend in a direction away from the first cap such that the second cap, the third cap, and the spray chamber are disengaged from the connector such that the first cap is still connected to the connector.

16. The connector safety shield of claim 15, wherein the connector safety shield is configured to allow the third cap to move in incremental steps towards the second cap and the spray chamber through engagement of the side arm with the plurality of the teeth on the hinge to thereby move the stopper in incremental distances within the spray chamber allowing the disinfectant to be sprayed on the distal end of the connector.

17. The connector safety shield of claim 15, wherein the hinge is comprised of an elastomer, the stopper is comprised of an isoprene, the spray chamber is comprised of high-density polyethylene, and the first cap, the second cap, the third cap, and the lock handle are comprised of polypropylene.

18. A connector safety shield configured to engage a connector, comprising:

a first cap comprising a closed top, an open bottom, and a sidewall extending between the top and the bottom defining an annular opening;

a second cap slidably engaged with said first cap comprising an open bottom defining an annular opening and a top defining an opening there through and a sidewall extending between the top and the bottom;

a spray chamber with an open top sealed by a stopper and a perforated bottom disposed within said second cap;

a third cap with an open top, an open bottom, and a sidewall extending between the top and the bottom defining a cylindrical opening wherein the third cap engages the connector and the bottom of the second cap;

a hinge comprising threads mounted to the third cap and operably connected to the first cap by a side arm extending from the sidewall of the first cap; and a center arm extending from the closed top of the first cap extending through the opening in the top of the second cap to engage the stopper positioned within the spray chamber configured to push disinfectant through the perforated bottom of the spray chamber onto the connector.

* * * * *